United States Patent
Choteau et al.

(10) Patent No.: US 6,190,416 B1
(45) Date of Patent: Feb. 20, 2001

(54) ORTHOPEDIC SURGERY ASSEMBLY FOR A HIP PROSTHESIS WITH A REMOVABLE NECK

(75) Inventors: Michel Choteau, Le Cateau; Gérard Grynblat, Bethune; Joël Letendart, Saint Saulve; Henri Mathevon, Dunkirk; Philippe Stahl, Sainghin en Melantois, all of (FR); Jacques Van Overschelde, Erpe Mere (BE); Philippe Vigier, Ascain (FR)

(73) Assignee: Groupe Grion, Saint Saulve (FR)

( * ) Notice: Under 35 U.S.C. 154(b), the term of this patent shall be extended for 0 days.

(21) Appl. No.: 09/142,834

(22) PCT Filed: Mar. 11, 1997

(86) PCT No.: PCT/FR97/00426

§ 371 Date: Feb. 8, 1999

§ 102(e) Date: Feb. 8, 1999

(87) PCT Pub. No.: WO97/33538

PCT Pub. Date: Sep. 18, 1997

(30) Foreign Application Priority Data

Mar. 12, 1996 (FR) .................................................. 96 03101

(51) Int. Cl.$^7$ ................................. A61F 2/36; A61F 2/46
(52) U.S. Cl. ................................... 623/22.12; 623/22.46; 606/85
(58) Field of Search ......................... 606/85; 623/22.12, 623/22.42, 22.46, 23 FOR

(56) References Cited

U.S. PATENT DOCUMENTS

| | | |
|---|---|---|
| 4,705,520 | 11/1987 | Ahrens . |
| 4,795,469 | 1/1989 | Oh . |
| 4,919,679 | 4/1990 | Averill et al. . |
| 4,963,155 | * 10/1990 | Lazzeri et al. ................... 606/85 X |
| 5,443,471 | 8/1995 | Swaiger . |

FOREIGN PATENT DOCUMENTS

| | | |
|---|---|---|
| 3147249 | 6/1983 | (DE) . |
| 4116507 | 9/1992 | (DE) . |
| 0000549 | 2/1979 | (EP) . |
| 0200672 | 11/1986 | (EP) . |
| 2575384 | 7/1986 | (FR) . |
| 2580926 | 10/1986 | (FR) . |
| 2693367 | 1/1994 | (FR) . |
| 2697996 | 5/1994 | (FR) . |
| 1371335 | 10/1974 | (GB) . |
| 2259859 | 3/1993 | (GB) . |

* cited by examiner

*Primary Examiner*—David H. Willse
(74) *Attorney, Agent, or Firm*—Wolf, Greenfield & Sacks, P.C.

(57) ABSTRACT

This orthopedic assembly has a connection between the ancillary tool and the stem or raspatory that allows both the raspatory and the femoral stem to be positioned in the intramedullary channel of a femur by means of the same ancillary tool. The connector includes a tapped hole extending from the bottom of a conical recess in the femoral end of the stem, or of the raspatory, and a threaded projection provided on the ancillary tool and designed to be screwed into the tapped hole. The bottom of the conical recess in the raspatory and in the stem has a profiled indentation whose edge includes alternating concave and convex curves and is designed to receive a male indexing part of a corresponding profile arranged on the end of the removable neck.

10 Claims, 3 Drawing Sheets

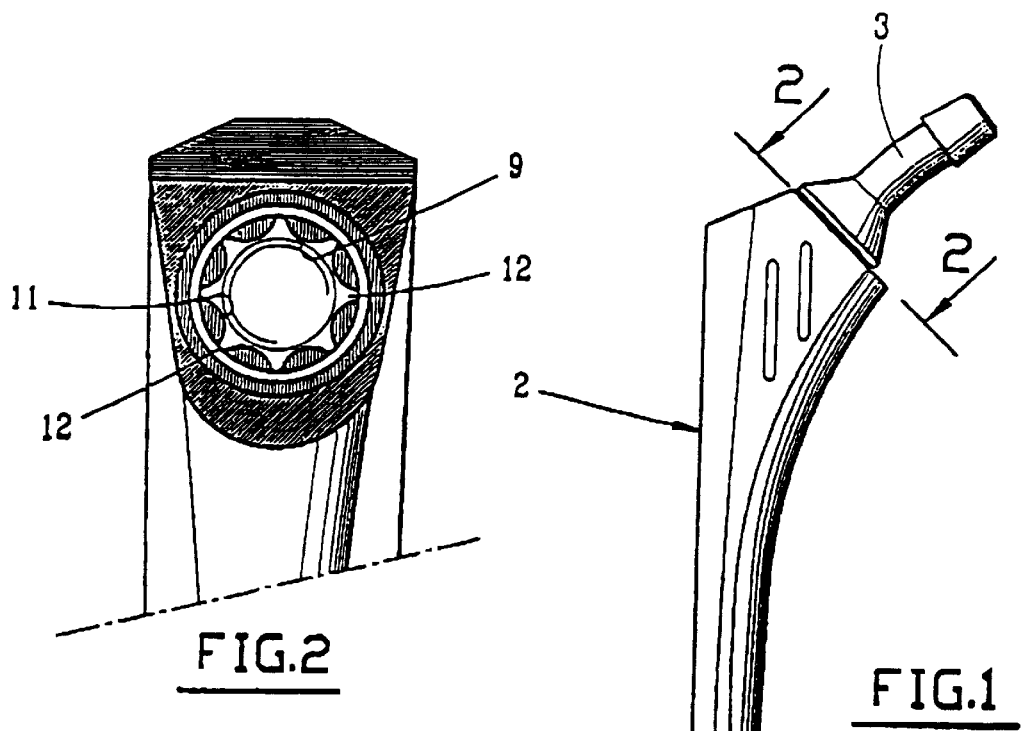
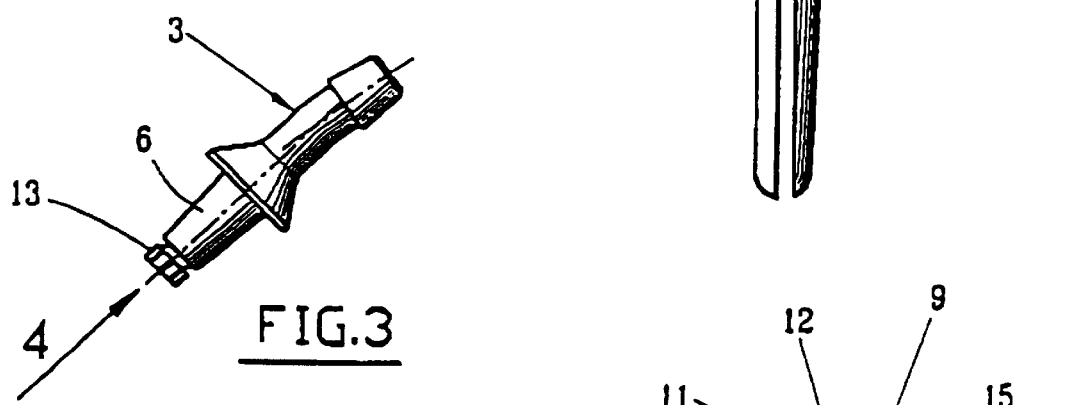
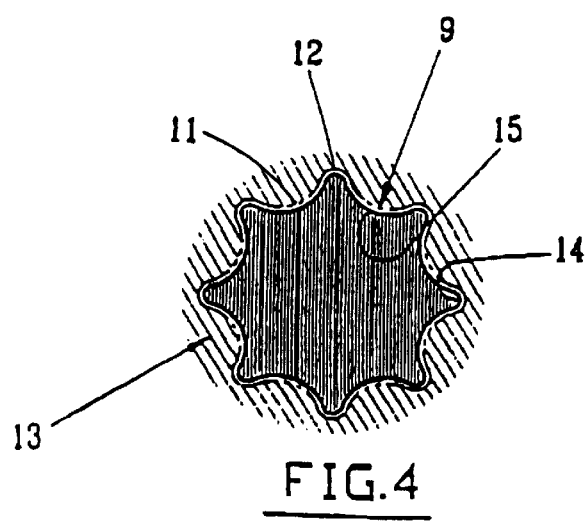

ORTHOPEDIC SURGERY ASSEMBLY FOR A HIP PROSTHESIS WITH A REMOVABLE NECK

The subject of the present invention is an orthopedic surgery assembly including an ancillary tool for a hip prosthesis, a femoral raspatory and a femoral stem of the type with a removable neck. This neck has a conical bearing span designed to engage in a matching conical recess formed in the proximal end of the stem. Stems of this type are described in particular by the patents FR A 8506214 (2580926) and 9214120 (2697996) and by the European patent EP-A-0017743.

Hip prostheses with removable necks are being increasingly used because of the great possibilities they give surgeons to allow them to adapt each prosthesis to the specific needs of their patients.

Although it is possible, as in the patent document U.S. Pat. No. 4,919,679, which describes a prosthesis with a fixed neck, to use a positioning ancillary tool whose axis is situated in the extension of the stem of the prosthesis, and is connected to the latter by connection means such as a thread, because the material volume in the proximal part of the stem is sufficient to permit the drilling and then tapping of a hole, this is no longer possible with prosthesis stems which are intended to receive removable necks. This is explained particularly by the fact that the connection hole is drilled obliquely in relation to the axis of the stem and in this way prohibits any operational drilling oriented in this axis.

The invention concerns a hip prosthesis with a removable neck and relates more particularly to the connection of the stem to the neck, and to all the advantages which derive from this connection. This is because, like any other prosthesis, a prosthesis of this kind must be easy to manipulate during positioning and requires the existence of a specific ancillary tool on account of the fact that mechanical engagement via the neck is no longer possible and since it is necessary for this engagement to be solid and firm so as to constitute a compact assembly between the ancillary tool and the stem. The same also applies to the raspatories which are used to prepare the medullary channel of the femur for receiving the prosthesis stem.

It is for this reason that the invention not only relates to a solid and firm connection of the prosthesis stem to its removable neck, rendering the assembly perfectly rigid and compact, but also to a specific ancillary tool for this type of prosthesis, also making it possible to form a perfectly rigid and compact assembly both with the prosthesis stem and with raspatories, in such a way as to provide the surgeon with reliable, simple and practical operating equipment.

As regards means for indexing a prosthesis with a removable neck, there is, for example, French Patent A 2 697 996 (Medinov) which provides an indexing indentation of the removable neck consisting of a succession of identical semicircular recesses adjacent to one another on the inner periphery of the bottom of the receiving hole. These recesses are necessarily situated facing in pairs and diametrically opposite each other in order to receive a transverse connecting rod which is integral with the removable neck and whose dimensions correspond to those of the indentations. These semicircular recesses thus form a circumferential alternation of concavities and ridges which means that said ridges are very fragile not only during manipulation of the neck in the indentation, but also during diverse mechanical stresses on the connection during the functioning of the prosthesis.

The invention makes use of the hole formed on the stem, for receiving the removable neck, in order to extend it along its axis to create indexing means and means of connection to an ancillary tool.

Means for possible extraction of the removable neck can also be provided in order to permit access again to said connection means. It must in fact be anticipated that a prosthesis may one day have to be extracted, or that the removable neck alone will need to be changed in favor of a neck of different dimensions.

According to the invention, the orthopedic surgery assembly comprises common means of connection between the ancillary tool and the stem and between the ancillary tool and the raspatory, allowing both the raspatory and the femoral stem to be positioned in the intramedullary channel of a femur by means of the same ancillary tool.

According to a preferred embodiment, the connection means include, on the stem, a tapped hole extending from the bottom of a recess for receiving the removable neck, and formed in the stem, and a threaded projection constituting one end of the ancillary tool and designed to be screwed into said tapped hole.

According to a complementary feature, these connection means also include, on the raspatory, a tapped hole extending from the bottom of a recess for receiving the removable neck, and formed in the proximal end of the raspatory, this tapped hole being designed to receive the threaded projection of the ancillary tool.

Thus, the invention makes use of the fact that the neck of the stem is removable, hence that the proximal end of the stem is provided with a recess for receiving this neck, in order to form in the bottom of this recess a means for connection to the ancillary tool; correspondingly, the invention provides for arranging in the proximal end of the raspatory, which is associated with this stem, a recess and a terminal connection means identical to those of the stem.

The ancillary tool advantageously includes an end which can be detached by rotation from its handle. This is because the latter is curved in shape and could not therefore be easily screwed or unscrewed in the operating field during the surgical intervention.

According to a second embodiment of the invention, the tapped hole is extended via an axial bore passing completely through the proximal part of the stem, and this assembly includes an ancillary tool for extracting the removable neck by introduction of an end part of this ancillary tool into the bore and into the tapped hole and by impaction on the end of the removable neck, said ancillary tool consisting of a rigid rod whose end part has a diameter which is slightly smaller than that of the introduction bore.

The ancillary tool is introduced through the cortical bone of the femur after first being targeted using a specific aiming device.

Compared to the technique previously used, the invention affords an appreciable advantage in terms of cost and simplification of the equipment.

According to another characteristic of the invention, the bottom of the recess in the raspatory and in the stem has a profiled indentation whose edge is made up of alternating concave and convex curves; a corresponding end of the neck includes a male indexing part provided with complementary alternating of convex and concave curves which can fit in the female concave and convex curves of the indentation in order to index the neck in a defined angular orientation.

Other features and advantages of the invention will become evident from the following description in which reference is made to the attached drawings which illustrate two embodiments by way of nonlimiting examples.

FIG. 1 is an elevation view, on a reduced scale, of a femoral stem of the removable neck type forming part of the orthopedic surgery assembly according to the invention.

FIG. 2 is a transverse sectional view, on an enlarged scale, along 2—2 in FIG. 1.

FIG. 3 is a longitudinal elevation view of the removable neck of the stem in FIGS. 1 and 2.

FIG. 4 is a transverse sectional view, on an enlarged scale, of the proximal end of the stem of FIGS. 1 and 2, showing in particular the recess at the end of the ancillary tool and the connection means between the latter and the stem.

Figure 5:
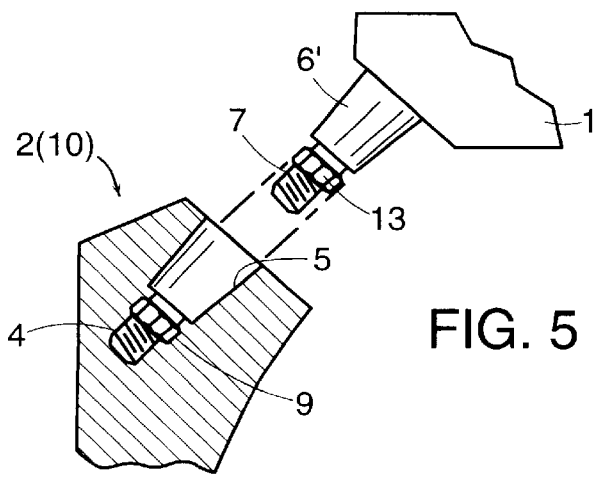
FIG. 5 is a sectional view of the proximal end of a stem or a raspatory, as well as a partial elevation view of the associated ancillary tool.
Figure 6:
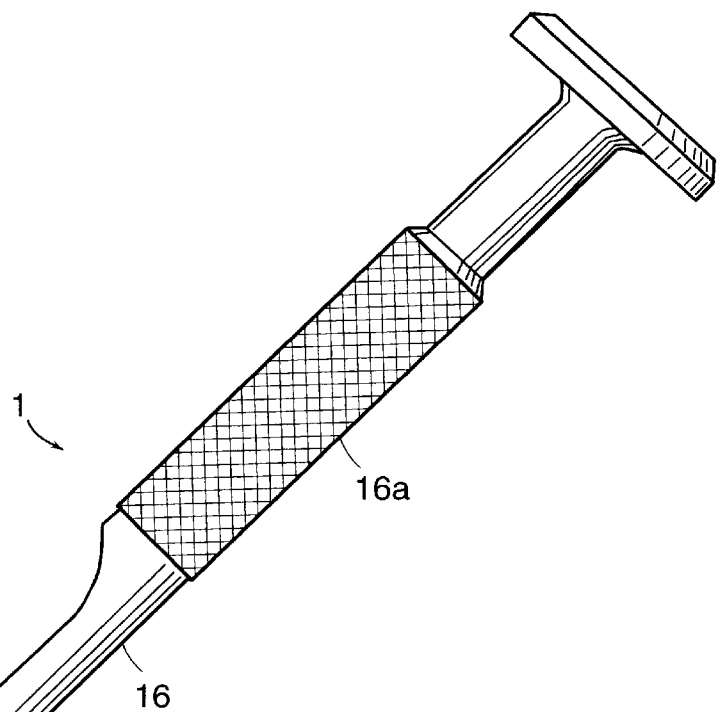
FIG. 6 is a longitudinal elevation view, on a reduced scale, of the ancillary tool forming part of the assembly according to the invention.

The orthopedic surgery assembly represented in the drawings comprises an ancillary tool 1 for a hip prosthesis, a femoral stem 2 of the type with a removable neck 3, and a femoral raspatory 10 which has approximately the same profile as the stem 2 and is provided, at its proximal end, with the same means of mechanical connection to the ancillary tool 1. A separate representation of such a raspatory is not therefore necessary, with the drawing in FIG. 4 representing the proximal end of both a stem 2 and a raspatory 10.

The surgical assembly with the three above-mentioned components 1, 2 and 10 comprises means of connection between the ancillary tool 1 and the stem 2 or the raspatory 10, allowing both the raspatory 10 and the femoral stem 2 to be positioned in the intramedullary channel of a femur by means of the same ancillary tool 1.

In the illustrative embodiment described, these connection means include a tapped hole 4 arranged in the bottom of a conical recess 5 in the proximal end of the stem 2. The conical surface of the recess 5 serves as a bearing surface for an end conical bearing span 6 of the neck 3 or span 6' of the ancillary tool 1 when the latter is connected to the stem 2 without its neck 3. Correspondingly, the end of the ancillary tool 1 is provided with a threaded projection 7 which can be screwed into the tapped hole 4 in order to connect the ancillary tool 1 and the stem 2.

This connection can be done in the same way in order to join the femoral raspatory 10 (FIG. 5) and the ancillary tool 1.

Thus, by virtue of its conical bearing span 6' and its threaded end 7, the same ancillary tool 1 can be connected to either the stem 2 or the femoral raspatory 10 by virtue of the connecting arrangement provided by the invention.

The bottom of the conical recess 5 of the raspatory 10 and of the stem 2 has a profiled indentation 9 which is arranged on the periphery of said bottom and whose edge is made up of alternating concave 12 and convex 11 curves. The corresponding end of the neck 3 includes a male indexing part 13 provided on its periphery with corresponding alternating convex 14 and concave 15 curves. These curves can engage respectively in the female concave curves 12 and the convex curves 11 in order to position the neck 3 in a defined angular orientation.

According to an advantageous embodiment, the indentation 9 and the male indexing part 13 comprise, respectively, a series of eight concave 12 and 15 and convex 11, 14 curves alternating about a circumference, the profile of the indexing part 13 being able to engage in the indentation 9 in any angular orientation.

The concave curves 15 of the male indexing part 13 have radii of curvature which are greater than the radii of curvature of its convex parts 14, interposed between the concave curves 15. The alternation of concave and convex curves and their different radii of curvature ensure a better distribution of the stresses than in the system in the patent FR-A 2 697 996, by omission of the ridges, while at the same time ensuring good indexing.

Thus, the concave parts 15 of the male element 13 have larger bearing surfaces than the convex parts 14. To give an illustrative numerical example, for eight concave curves 15 alternating with eight convex curves 14, the respective radii of curvature are advantageously between approximately 1.40 and 1.60 mm and 0.40 to 0.50 mm, with preferred values of 1.55 mm and 0.45 mm. Thus, the ratio of the radii of the concave curves 15 to the radii of the convex curves 14 is approximately 1:3.

The profiles of the indentation 9 and of the complementary angular indexing part 13 have a mechanical strength which is greater than that of the rose shape in FR-A-2697996 by virtue of the alternation of concave and convex surfaces and the corresponding omission of pointed zones. This arrangement therefore increases the mechanical strength of the connection between the removable neck and the stem 2 or raspatory 10. This increase in strength is also due to the presence of two alternating concave and convex surfaces on the indentation 9 and on the indexing part 13, which complement one another, which is not the case with the corresponding surfaces in FR-A-2697996.

The ancillary tool 1 comprises a handle 16 which is provided with a knurled zone 16a for gripping manually, and from which the threaded projection 7 can be detached by rotation. More precisely, the projection 7 is mounted axially inside a socket having the conical bearing span 6', free in rotation and movable in translation, the socket being integral with an end part 17 of the handle 16 curved in relation to the rest of the handle.

The threaded projection 7 passes right through the end part 17 and is provided with a knob 18 for gripping manually, allowing the projection 7 to be screwed into the tapped hole 4.

By virtue of this arrangement, the projection 7 can be screwed or unscrewed without at the same time having to turn the handle 16 in the operating field, which would be inconvenient because of its non-rectilinear end.

The recess 5 and the hole 4 are protected by the removable neck 3, which offers the surgeon the advantage of being able to introduce the end of the ancillary tool 1 therein after extracting the removable neck 3, without the need to put in place a cap for protecting the tapped volume 4, as is the case in some known prostheses. The reason is that the presence of the neck affords this protective function.

Figure 7:
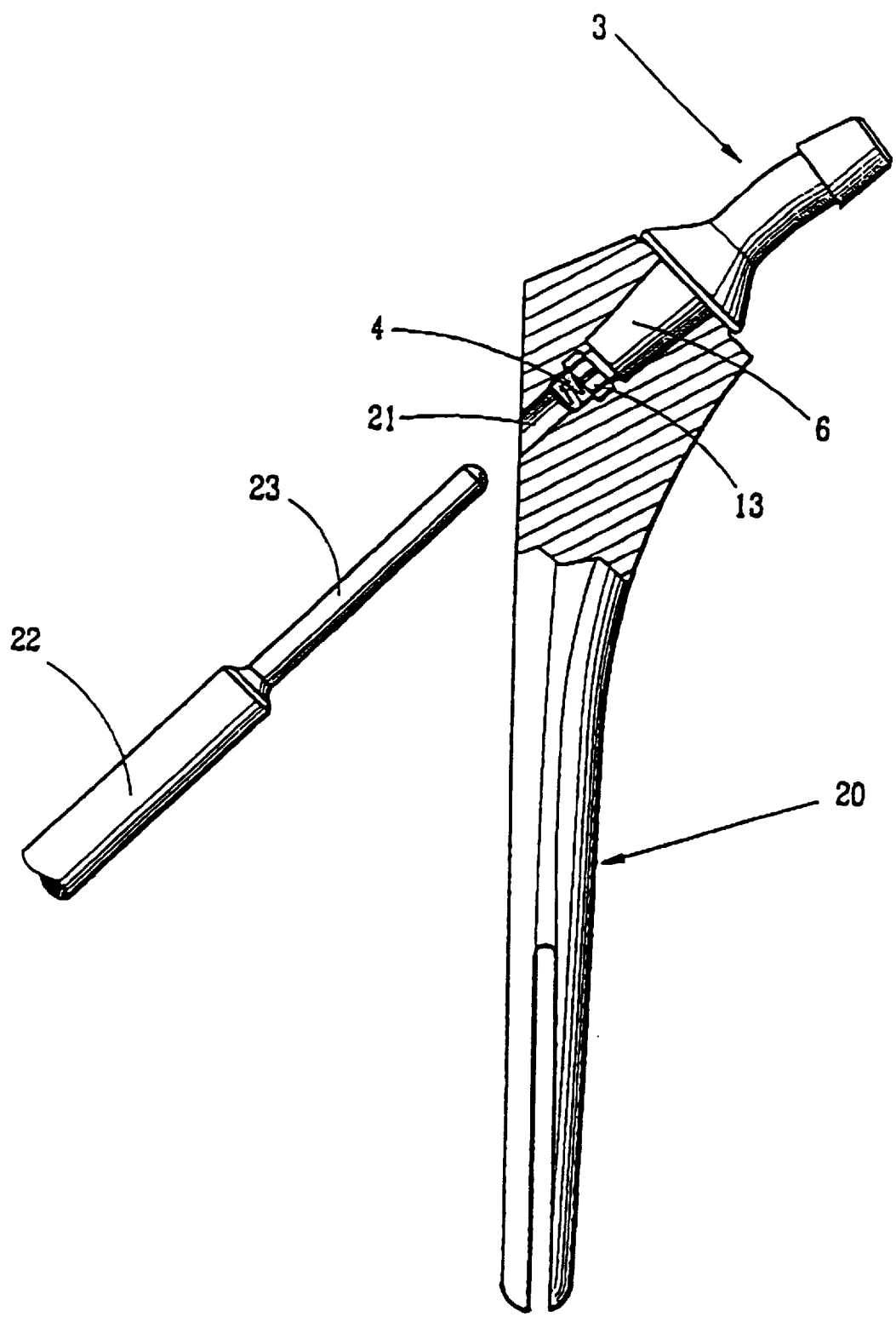
FIG. 7 is an exploded perspective view, with partial sectioning, of a second embodiment of the femoral stem and of the ancillary tool according to the invention.

FIG. 7 shows a second embodiment of the femoral stem 20: its tapped hole 4 is extended via an axial bore 21 passing completely through the proximal part of the stem 20. Associated with this stem 20 there is an ancillary tool 22 consisting of a rigid rod including an end part 23 whose diameter is slightly smaller than that of the introduction bore 21. The neck 3 can be extracted from the recess 5 and the indentation 9 by impacting the end of the end part 23 of the ancillary tool 22 on the male part 13.

The bore 21 can be closed off by a plug (not shown) made of a biocompatible product such as polyethylene. This plug can be removed by impaction at the same time as the removable neck 3.

What is claimed is:

1. An orthopedic surgery assembly including an ancillary tool for a hip prosthesis, a femoral raspatory and a femoral stem with a proximal end and a removable neck having a bearing span designed to engage a matching recess formed in the proximal end of the stem, said assembly comprising a tapped hole disposed on the stem and extending from a bottom of the recess on the stem for receiving the removable neck, and a threaded projection being formed on one end of the ancillary tool and being structured to be screwed into the tapped hole, both the raspatory and the femoral stem being structured to be positioned in an intramedullary channel of a femur using the same ancillary tool.

2. The assembly according to claim 1 further comprising, a tapped hole extending from a bottom of a recess for receiving the removable neck, and being formed in the proximal end of the raspatory, the tapped hole in the raspatory being designed to receive the threaded projection of the ancillary tool.

3. The assembly according to claim 2, wherein the bottom of the recess in the raspatory and in the stem has a profiled indentation having an edge made up of circumferential alternating female concave and convex curves, and wherein a corresponding end of the neck includes a male indexing part provided with complementary circumferential alternating convex and concave curves which are structured to fit in the female concave and convex curves of the indentation to position the neck in a defined angular orientation.

4. The assembly according to claim 3 wherein the indentation and the male indexing part of the neck comprise a series of eight convex and concave curves alternating about a circumference.

5. The assembly according to claim 3, wherein the male indexing part of the neck has concave curves with radii of curvature greater than radii of curvature of the convex curves interposed between said concave curves.

6. The assembly according to claim 5, wherein for eight concave curves alternating with eight convex curves, the respective radii of curvature are between approximately 1.40 and 1.60 mm and 0.40 to 0.50 mm, and wherein a ratio of the radii of curvature of the concave curves to the radii of curvature of the convex curves is approximately 1:3.

7. The assembly according to claim 1 wherein the ancillary tool comprises a handle from which the threaded projection can be detached by rotation.

8. The assembly according to claim 7, wherein the threaded projection is rotatably mounted and movable in a socket integral with an end part of the handle and has the bearing span of the neck, and wherein the threaded projection passes right through said end part of the handle and is provided with a knob for gripping manually.

9. The assembly according to claim 1 wherein the tapped hole is extended via an axial bore passing completely through the proximal end of the stem, and wherein the assembly further includes a second ancillary tool for extracting the removable neck by introduction of an end part of the second ancillary tool into the axial bore and into the tapped hole and by impaction on an end of the removable neck, said second ancillary tool comprising a rigid rod including the end part, the end part having a diameter slightly smaller than a diameter of the axial bore.

10. The assembly according to claim 9, wherein the axial bore is closed by a plug made of a biocompatible material.

* * * * *